United States Patent [19]

Regtien

[11] Patent Number: 4,626,774
[45] Date of Patent: Dec. 2, 1986

[54] METHOD AND ARRANGEMENT FOR MEASURING THE CONTAMINATION OF A CAPACITIVE DEW-POINT SENSOR

[75] Inventor: Paulus P. L. Regtien, Delft, Netherlands

[73] Assignee: Endress u. Hauser GmbH u. Co., Fed. Rep. of Germany

[21] Appl. No.: 523,464

[22] Filed: Aug. 16, 1983

[30] Foreign Application Priority Data

Aug. 27, 1982 [DE] Fed. Rep. of Germany ....... 3231995

[51] Int. Cl.$^4$ ........................................... G01R 27/26
[52] U.S. Cl. .................................... 324/61 R; 374/28
[58] Field of Search ............ 324/61 R, 65 R; 73/335, 73/336, 336.5, 338, 338.3; 338/35; 340/602; 374/28, 21; 236/44 C; 62/176.1

[56] References Cited

U.S. PATENT DOCUMENTS 2,435,895  2/1948  McIlvaine .......................... 324/65 R
3,664,192  5/1972  Campbell et al. .................. 73/336.5

FOREIGN PATENT DOCUMENTS 0973614  8/1975  Canada .............................. 324/61

OTHER PUBLICATIONS

Whitehaus, Linearizing Relative Humidity Measurements, 9-1972, pp. 72-73.

Primary Examiner—Reinhard J. Eisenzopf
Assistant Examiner—Jack B. Harvey
Attorney, Agent, or Firm—Gerald J. Ferguson, Jr.; James E. Bryan; Michael P. Hoffman

[57] ABSTRACT

A dew-point measuring instrument has a capacitive dew-point sensor 1 which is cooled by a cooling device 17 to the dew-point temperature measured by a temperature sensor 8. A phase measuring circuit 14 measures the phase angle of the impedance of the capacitive dew-point sensor 1. The measured phase angle is used as a gauge for the contamination of the dew-point sensor 1.

6 Claims, 3 Drawing Figures

METHOD AND ARRANGEMENT FOR MEASURING THE CONTAMINATION OF A CAPACITIVE DEW-POINT SENSOR

The invention relates to a method for measuring the contamination of a capacitive dew-point sensor and to an arrangement for carrying out the method.

Capacitive dew-point sensors are used in dew-point measuring instruments to determine the occurrence of the dew covering on the condensation surface on reaching the dew-point temperature. Their effect is based on the fact that the sensor capacitance alters considerably during the formation of a dew layer owing to the high dielectric constant of water. The capacitance and therefore the thickness of the dew layer can be kept at a predetermined constant value by temperature control. The temperature of the condensation surface measured by a temperature sensor is then the dew-point temperature.

The accuracy of measurement of such capacitive dew-point sensors decreases as the contamination of the sensor surface increases. This is due to the vapour pressure reduction and non-homogeneous dew formation. The condensation surface of the dew-point sensor therefore has to be cleaned from time to time. However, as it is difficult to determine the degree of contamination, there is a risk that errors in measurement which increase unnoticeably over a prolonged period might occur or that the measurement of dew-point is interrupted unnecessarily often if cleaning takes place too frequently.

The object of the invention is to propose a method of continuously measuring the contamination of a capacitive dew-point sensor without disturbing or interrupting the measurement of dew-point.

This is achieved according to the invention in that the phase angle of the sensor impedance occurring during dew formation is measured and is used as a gauge of contamination.

The invention is based on the fact that the phase angle of the sensor impedance varies as a function of the degree of contamination of the dew-point sensor. In the dry state, the impedance of the dew-point sensor, independently of the degree of contamination, is virtually a purely capacitive reactance so that the sensor impedance has the phase angle $\phi = -90°$. If a water layer forms on the dew-point sensor, the phase angle depends on the electrical conductivity of the water. With pure water, the phase angle $\phi = -90°$ essentially remains. This condition arises if the dew covering is formed on a completely clean condensation surface. On the other hand, if the condensation surface is contaminated, the contaminants dissolve in the water in the dew covering, making the water electrically conductive. The higher the conductivity, the smaller the phase angle $\phi$ of sensor impedance.

Measurement of the phase angle of the sensor impedance as a gauge of the contamination of the dew-point sensor produces a signal which varies analogously with the degree of contamination. Measurement can be carried out continuously, simultaneously with dew-point measurement, without dew-point measurement being impaired by it in any way. Measurement of contamination is essentially independent of other influencing variables such as dew-point temperature, gas temperature, dew-point distance and air speed.

It has also been found that for measuring frequencies which are not too high, the phase angle $\phi$ of the sensor impedance is independent of the quantity of water, i.e. of the thickness of the dew layer. Moreover, the influence of the thickness of the dew layer is not disturbing even at higher frequencies as a dew layer of constant thickness is usually adjusted by temperature control so that a clear result is also obtained for the correlation between phase angle and degree of contamination.

On the other hand, it has been found that the absolute value of sensor impedance is a gauge of the quantity of water, i.e. for the thickness of the dew layer. An advantageous embodiment of the method according to the invention therefore involves measuring the absolute value of the sensor impedance as a gauge for the thickness of the dew layer.

An arrangement for carrying out the method according to the invention is characterised in the sub-claims.

Other features and advantages of the invention are mentioned in the following description of an embodiment with reference to the drawings.

Figure 1:
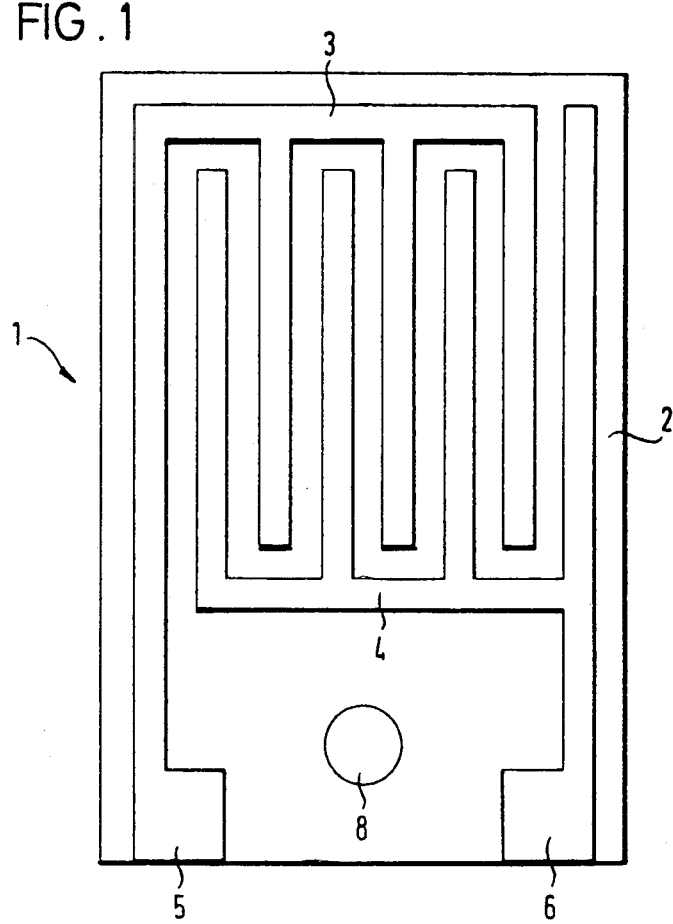
FIG. 1 shows a plan view of a capacitive dew-point sensor of the thin film type.
Figure 2:
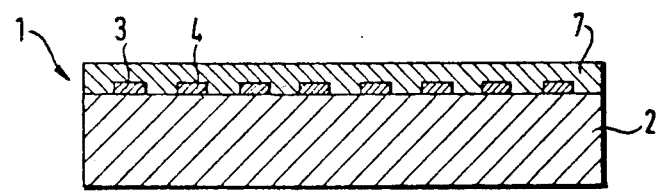
FIG. 2 shows a sectional view of the dew-point sensor in FIG. 1.

The capacitive dew-point sensor 1 shown in a plan view in FIG. 1 and in section in FIG. 2 has a substrate 2 on whose surface two intermeshing comb electrodes 3 and 4 are formed by the thin film method. The substrate 2 consists of an insulating material which is insensitive to moisture, preferably a ceramic material. Contact surfaces 5 and 6 which permit the connection of an external measuring circuit are moulded on the comb electrodes 3, 4. The surface of the substrate 2 bearing the comb electrodes 3, 4 is covered with a protective layer 7 consisting, for example, of glass. A temperature sensor 8 for measuring the temperature of the dew-point sensor is also arranged on the upper side of the dew-point sensor. The temperature sensor can be, for example, the measuring resistor of a resistance thermometer.

When using such a capacitive dew-point sensor in a dew-point measuring instrument, the dew-point sensor is cooled by a suitable cooling device, as known, until dew is deposited on the surface of the protective layer 7. The capacitance between the comb electrodes 3 and 4 measured on the contact surfaces 5 and 6 alters due to the formation of the dew layer owing to the high dielectric constant of water. The alteration in capacitance demonstrates the attainment of the dew-point temperature which is measured and displayed by means of the temperature sensor 8. A temperature control device is usually provided for monitoring the cooling device so as to maintain a dew layer of constant thickness. The dew-point sensor is thus constantly maintained at the dew-point temperature which can be displayed permanently by means of the temperature sensor 8.

The accuracy of measurement of the dew-point sensor is impaired if the surface of the glass layer 7 forming the condensation surface is contaminated because the contamination can lead to a reduction in vapour pressure and to non-homogeneous dew formation.

Figure 3:
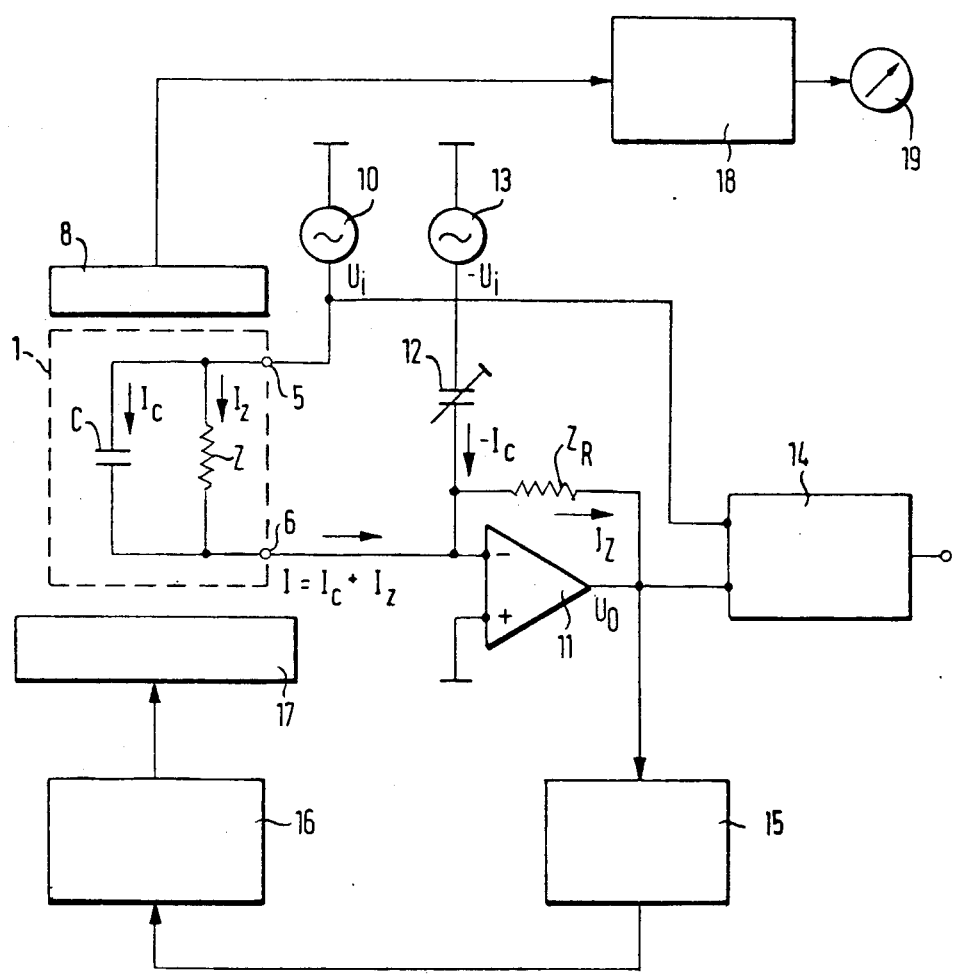
FIG. 3 shows a schematic circuit diagram of a dew-point measuring instrument with a capacitive dew-point sensor and with an arrangement for measuring the contamination of the dew-point sensor.

FIG. 3 shows the circuit diagram of a dew-point measuring instrument which enables the contamination of the dew-point sensor to be measured in addition to the dew-point temperature.

The equivalent circuit diagram of the dew-point sensor is shown in the box 1 indicated in broken lines. The capacitor C represents the capacitance of the dew-point sensor which appears in the dry state between the contact surfaces 5 and 6 and is virtually loss-free. Once a dew layer has formed on the dew-point sensor, the impedance Z of the dew layer lies parallel to this capacitance C and represents a loss-afflicted capacitance whose loss factor depends on the electrical conductivity of the water which, in turn, is caused by the contamination present on the condensation surface which dissolves in the water.

The contact surface 5 is connected to one terminal of an AC voltage source 10 whose other terminal is earthed. The contact surface 6 is connected to the inverting input of an operational amplifier 11 whose non-inverting input is earthed and in whose feedback branch a reference impedance $Z_R$ lies.

The inverting input of the operational amplifier 11 is also connected to one terminal of an adjustable compensation capacitor 12 whose other terminal is connected to an AC voltage source 13 which supplies an antiphase AC voltage $-U_i$ of equal amplitude, to the AC voltage $U_i$ of the AC voltage source 10.

The output of the operational amplifier 11 is connected to one input of a phase measuring circuit 14 which receives at its other input the voltage $U_i$ of the AC voltage source 10 as phase reference variable. The phase measuring circuit 14 emits at its output a signal which is dependent on the phase shift between its input voltages.

A signal processing circuit 15 whose output signal is fed to a temperature controller 16 is also connected to the output of the operational amplifier 11. Temperature controller 16 controls a cooling device 17 which cools the dew-point sensor 1. FIG. 3 again shows the temperature sensor 8 which is connected to a temperature measuring circuit 18 which emits a signal which is dependent on the temperature of the dew-point sensor 1 and is displayed by means of a display device 19.

If it is assumed that a dew layer has formed on the dew-point sensor, the impedance Z of the dew layer is also present in addition to the dry capacitance C. The voltage source 10 transmits via the total impedance of the dew-point sensor 1 to the inverting input of the operational amplifier 11 a current which is composed of the current $I_C$ flowing via the capacitance C and the current $I_Z$ flowing via the impedance Z of the dew layer:

$$I = I_C + I_Z.$$

The compensation capacitor 12 is adjusted in such a way that its capacitance is equal to the dry capacitance C of the dew-point sensor 1. The voltage source 13 therefore transmits via the compensation capacitor 12 a current $-I_C$ which compensates the current $I_C$ coming from the dew-point sensor 1. It is only the current $I_Z$ which is inversely proportional to the impedance Z which flows via the reference impedance $Z_R$.

The output voltage $U_O$ of the operational amplifier 11 therefore assumes the following value:

$$U_o = -U_i(Z_R/Z).$$

The voltage $U_O$ therefore has a value which is inversely proportional to the value of the impedance Z, and it has a phase shift dependent on the phase angle of the impedance Z, relative to the voltage $U_i$. This phase shift can be equal to the phase angle of the impedance Z if the phase angle of the reference impedance $Z_R$ is suitably calculated.

If the impedance of the dew layer is written in the complex form $$Z = R + jX$$

wherein R represents the real portion and X the imaginary portion of the impedance, the phase angle of the impedance Z is known to be defined by the following equation $$\phi = arctg.(X/R).$$

If the condensation surface of the dew-point sensor is completely clean, the water in the deposited dew layer remains electrically non-conductive and the impedance Z is virtually a pure capacitance which lies parallel to the dry capacitance C. The real portion of the impedance Z is $R = 0$, and the phase angle of the impedance Z has the value $\phi = -90°$. As the contamination of the dew-point sensor increases, the electrical conductivity of the water in the dew layer increases and the real portion R of the impedance of the dew layer consequently increases so that the absolute value of the angle $\phi$ becomes smaller. Consequently, the phase shift between the output voltage $U_O$ of the operational amplifier 11 and the input voltage $U_i$ also varies. This alteration in the phase shift is indicated by the output signal of the phase measuring circuit 14 which is therefore a gauge of the contamination of the dew-point sensor 1.

If the frequency of the AC voltage source 10 is not too high, the phase angle $\phi$ is essentially independent of the quantity of water located on the dew-point sensor.

The fact that the amplitude of the output voltage $U_O$ of the operational amplifier 11 depends on the absolute value of the impedance Z, is utilised in the illustrated circuit for carrying out dew-point measurement so that no special capacitance measuring circuit is needed. The amplitude of the voltage $U_O$ is inversely proportional to the absolute value of the impedance Z which is desirable because the absolute value of the impedance Z varies inversely with the thickness of the dew layer, i.e. diminishes as the thickness of the dew layer increases. The amplitude of the voltage $U_O$ therefore alters as a function of the thickness of the dew layer in the same direction as the output signal of the capacitance measuring circuits normally used in dew-point measuring instruments, namely in the same direction as the thickness of the dew layer. Therefore, if the signal processing circuit is designed in such a way that it emits an output signal proportional to the amplitude of the voltage $U_O$, this output signal can be used in the same manner as the output signal of a conventional capacitance measuring circuit for controlling the temperature of the dew-point sensor.

The signal processing circuit 15 can therefore be a simple rectifier circuit which transmits a DC voltage proportional to the amplitude of the voltage $U_O$ to the temperature controller 16.

If the dew-point sensor 1 has not yet cooled to the dew-point temperature, only the dry capacitance C exists which, however, is compensated by the compensation capacitor 12 so that the output voltage $U_O$ has the value zero. The temperature controller 16 is thus caused to control the cooling device 17 in such a way that the dew-point sensor 1 is gradually cooled. When the dew-point temperature is attained and a dew layer formed on the dew-point sensor, the output voltage $U_O$ increases and the temperature controller 16 controls the cooling device 17 in such a way that the dew-point sensor 1 is kept at a temperature which corresponds to a predetermined amplitude of the output voltage $U_O$, i.e. to a predetermined size of the absolute value of impedance Z. This temperature is the dew-point temperature which is determined by the temperature sensor 8 and is displayed by the display device 19.

The output signal from the phase measuring circuit 14 can be used to trigger an alarm or an automatic cleaning process if the contamination exceeds a predetermined limit value. To a limited extent it is also possible to correct the measured dew-point value on the basis of the output signal from the phase measuring circuit.

The compensation of the dry capacitance C effected by the compensation capacitor 12 and the voltage source 13 is not absolutely essential as the phase and absolute value of impedance Z as well as the phase and absolute value of total impedance of the dew-point sensor including the dry capacitance C depend on the contamination of the dew-point sensor. However, the compensation illustrated in FIG. 3 makes the measurement of contamination more accurate and more sensitive. A particular advantage of the circuit shown in FIG. 3 lies in the fact that measurement is independent of the impedance of the connecting cable between the dew-point sensor 1 and the measuring circuit as the cable impedance lies between the two inputs of the operational amplifier 11.

I claim:

1. A method of measuring the contamination of a capacitive dew-point sensor; said dew-point sensor comprising a substrate; means for cooling said substate; capacitive electrodes arranged on said substrate, said capacitive electrodes having an impedance which varies in response to the presence of dew on said substrate, said impedance having a phase angle which varies in response to the degree of contamination of said dew-point sensor; means for measuring said impedance between said electrodes upon the formation of dew on said substrate; means for measuring the phase angle of said impedance; and means for indicating the temperature of said substrate; said method comprising: measuring the phase angle of said impedance upon the formation of dew on said substrate and using the measured phase angle as a measure of the contamination of the dew-point sensor.

2. A method as claimed in claim 1, comprising the further step of measuring the absolute value of said impedance as a measure of the thickness of the dew layer.

3. A method as claimed in claim 1 or 2 comprising the further step of compensating the capacitance of said capacitive electrodes occurring in the dry state.

4. Apparatus for measuring dew-point temperature and contamination of a capacitive dew-point sensor comprising:
 a capacitive dew-point sensor including a substrate and capacitive electrodes disposed on said substrate;
 means for measuring the impedance between said electrodes, said impedance varying in response to the formation of said dew on the substrate;
 means reponsive to the amplitude of said impedance for measuring the temperature at which said dew forms on the substrate and thus measure said dew-point temperature; and
 means responsive to the phase angle of said impedance for measuring said contamination of the dew-point sensor.

5. Apparatus as in claim 4 where said means for measuring the impedance between said electrodes includes (a) a first AC voltage source connected to one of said electrodes and (b) an operational amplifier having a feedback path with a reference impedance connected in the feedback path, said operational amplifier having one input thereof connected to the other of said electrodes and being responsive to said AC source to develop at the output thereof said impedance between the electrodes and where said means for measuring the contamination of the dew includes a phase measuring circuit having a first input connected to said first AC voltage source and a second input connected to the output of said operational amplifier to thus measure said phase of the impedance between the electrodes.

6. Apparatus as in claim 5 including impedance cancellation means for cancelling the impedance between said electrodes prior to said formation of the dew on the substrate from the impedance measured by said means for measuring the impedance between the electrodes, said impedance cancellation means including a second AC voltage source in antiphase to said first AC voltage source and an adjustable capacitor connected between said second AC voltage source and said one input of the operational amplifier where adjustments of the latter capacitor effects said cancellation of the electode impedance prior to said formation of the dew from said measured impedance.

* * * * *